United States Patent [19]

Funke

[11] Patent Number: 4,987,897
[45] Date of Patent: Jan. 29, 1991

[54] BODY BUS MEDICAL DEVICE COMMUNICATION SYSTEM

[75] Inventor: Hermann D. Funke, Bonn, Fed. Rep. of Germany

[73] Assignee: Medtronic, Inc., Minneapolis, Minn.

[21] Appl. No.: 408,811

[22] Filed: Sep. 18, 1989

[51] Int. Cl.$^5$ .............................................. A61N 1/00
[52] U.S. Cl. .......................... 128/419 PG; 128/419 D
[58] Field of Search ............. 128/419 D, 419 PG, 421

[56] References Cited

U.S. PATENT DOCUMENTS

| | | | |
|---|---|---|---|
| 3,952,750 | 4/1976 | Mirowski | 128/419 D |
| 4,146,029 | 3/1979 | Ellinwood | 128/260 |
| 4,543,955 | 10/1985 | Schroeppel | 128/419 PG |
| 4,550,370 | 10/1985 | Baker | 128/419 PG |
| 4,787,389 | 11/1988 | Tarjan | 128/419 PG |
| 4,793,353 | 12/1988 | Borkan | 128/421 |
| 4,886,064 | 12/1989 | Strandberg | 128/419 PG |

Primary Examiner—Lee S. Cohen
Assistant Examiner—Scott M. Getzow
Attorney, Agent, or Firm—Reed A. Duthler

[57] ABSTRACT

A system intended for being at least partly implanted into a living body and comprising at least two modules or devices which are interconnected by a communication transmission channel, at least one of said modules being provided with transmitting and receiving means for a bidirectional exchange of information with at least one further module and at least one other module of which being provided at least with receiving means or transmitting means for receiving information from at least one further module or for transmitting information to at least one further module, respectively. Within the intracorporal region, said communication transmission channel is wireless. It includes the ion medium of the intra and extracellular body liquids and provides for an electrolytic-galvanic coupling between two or more implantable modules and/or between at least one implantable module and external skin electrodes intended for connection to an external module. The exchange of information is effected by modulated medium frequency signals in the frequency range from 10 to 100 kHz which signals are passed through said communication transmission channel.

31 Claims, 5 Drawing Sheets

BODY BUS MEDICAL DEVICE COMMUNICATION SYSTEM

BACKGROUND OF THE INVENTION

1. Field of the Invention

This invention relates to a system of medical devices intended for being at least partly implanted into a living body and comprising at least two modules which are interconnected by a communication transmission channel denoted the 'body bus'.

2. Description of the Prior Art

Devices of this type are known in different embodiments, e.g. EPO 0 011 935 and EPO 0 011 936 describe an external programming device and an implantable electromedical device adapted for being programmed thereby, wherein the programming device comprises a transmitting antenna, and the implantable device comprises a receiving antenna which are mutualy aligned with each other for programming in order to transcutaneously transmit high frequency programming signals in the form of electromagnetic waves from the transmitting antenna to the receiving antenna. In view of the fact that high frequency electromagnetic waves are heavily attenuated or screened by body tissue, the implanted receiving antenna must be exactly located for programming. Such a procedure is particularly troublesome if a plurality of programmable modules, e.g. a pacemaker, a defibrillator and a drug dispensing device, are implanted, the receiving antennas of which must be individually located.

In the case of a prior muscle stimulation apparatus (U.S. Pat. No. 4,524,774) in a similar manner, muscle potentials detected by implanted sensors are converted by a modulator into control signals for a telemetry transmitter which is integrated into the respective sensor. This telemetry transmitter transcutaneously transmits high frequency telemetry signals to an external telemetry receiver which is connected to a data processing unit. The latter, on the base of the received signals, controls a likewise externally disposed telemetry transmitter for delivering high frequency control signals, against transcutaneously, to receivers of implanted muscle stimulators. The transcutaneously transmitted signals are in the megacycles/sec. frequency range so that the aforementioned restrictions are encountered in this case too.

Furthermore, it is known (FIG. 1 of U.S. Pat. No. 4,543,955) to transmit measuring signals of an implanted sensor module through a wire connection to another implanted module, such as a pacemaker or a drug delivery device. This requires, during implantation, a troublesome wiring of connection conduits. Furthermore if an infection occurs at one of the implanted modules, all modules and connection conduits must be removed because the infection can spread along the connection conduits. In conformity with modified embodiments of the last mentioned device (FIGS. 2 and 5 of U.S. Patent 4,543,955) measuring signals, which have been converted into a program code, also can be unidirectionally transmitted, in a wireless manner, from the sensor to the pacemaker or to the drug dispensing device, wherein either the signals defining the program code are directly transmitted through body tissue (i.e., without any carrier) or again a high frequency transmitter is used. A carrier free signal direct transmission, for being effective, must be carried through during the refractory phases, i.e. must be synchronized with the heart cycle because otherwise the signals required for such a direct transmission may provoke undesired biological reactions. On the other hand, the high frequency transmission, in this case too, poses problems because of the heavy attenuation caused by body tissue and is possible, if at all, merely if the transmitting and receiving antennas are closely spaced with in the body.

In addition, it is known from U.S. Pat. No. 4,787,389 to provide implantable defibrillator-pacemaker system where the defibrillator's operation is controlled by the separately implanted pacemaker. Signal transmission is effected by coded pulse trains as in U.S. Pat. No. 4,593,955.

SUMMARY OF THE INVENTION

The object basic to the invention is to provide for a device of the type mentioned at the beginning which allows a signal transmission between the modules in a particularly simple, reliable and universally applicable manner while simultaneously avoiding the above discussed deficiencies.

In conformity with the invention, this object is reached by a system intended for being at least partly implanted into a living body and comprising at least two medical devices or modules which are interconnected by a communication transmission channel, at least one of said modules being provided with transmitting and receiving means for a bidirectional exchange of information with at least one further module and at least one other module of which being provided at least with receiving means or transmitting means for receiving information from at least one further module or for transmitting information to at least one further module, respectively, wherein within the intracorporal region said communication transmission channel is wireless, includes the ion medium of the intra and extracellular body liquids and provides for an electrolytic-galvanic coupling between two or more implantable modules and/or between at least one implantable module and external skin electrodes intended for connection to an external module and wherein the exchange of information is effected by modulated medium frequency signals in the frequency range from 10 to 100 kHz which signals are passed through said communication transmission channel by direct conduction.

A modulated signal in the frequency range from 10 kHz to 100 kHz has a sufficiently high frequency to not cause any polarization problems within the living body and to allow an effective filtering with high Q filters requiring only little installation space. On the other hand, this frequency range is so low that undesired high frequency phenomena, such as radiation problems, crosstalk and excessive attenuation of the desired signals by the body tissue are avoided. Rather, modulated signals in the frequency range from 10 to 100 kHz are electrolytically-galvanically transmitted over the distances encountered in the living body with such a low attenuation that on the transmitter side signal amplitudes which biologically are certainly ineffective and which can be transmitted without any regard to the heart cycle also to electrodes which might be provided for stimulation of the heart are sufficient to allow the modulated signals to be reliably detected at the receiver side at low expenditure for filters and amplifiers.

A bidirectional exchange of information provides for an interactive mutual coupling of the individual modules. The functional interconnection between implanted and external modules may be obtained in a particularly simple manner via body fluids by making use of the electrolytical-galvanical coupling, presently also shortly named body bus, and via the skin electrodes so that a troublesome search for the antennas of the implanted module or modules is avoided.

In conformity with a further development of the invention, at least one digitally programmable implantable module and an external module in the form of a programming device are provided. The programmer would, because of the body bus bidirectional properties, enable interactive intelligent programming. Over a modem, telephone programming and control would be possible, especially a necessity for endangered tachy or defibrillator patients.

Preferred examples of implanted modules are nerve stimulators, muscle stimulators, cardiac pacemakers, defibrillators, drug dispensing devices, sensors for detecting body parameters or body activities as well as controllable and/or programmable artificial organs. Apart from the aforementioned programming devices, particularly, but not exclusively, monitoring and/or test devices may be used as external modules such as data recording devices (magnetic tape devices or the like) or modems adapted for connection to telephone circuits.

If a plurality of implantable modules are provided, programming and/or intelligent decision means, in conformity with a further development of the invention, preferably are concentrated in one of the implanted modules only wherein, in case of need, other implanted modules can be indirectly programmed via said one module. Thereby it is possible to keep the hardware expenditure, the weight, the space requirements and the energy consumption of the total of implanted modules particularly small. Basically, however, it is likewise possible to provide a plurality of implanted modules comprising programming and/or intelligent decision means which modules mutually communicate via the body bus.

Preferably the modules are provided with means for receiving and/or transmitting of pulsecode-modulated medium frequency signals. Al-modulated medium frequency signals may be used, i.e. the signal has a single, fixed frequency of e.g., 30 kHz, and this signal, at the transmitting side, is switched on and off as a function of the modulation. In conformity with a modified embodiment, the modules may be provided with means for receiving and/or transmitting signals which are frequency shifted between a pair of frequencies within the medium frequency range. That means a pair of predetermined fixed signal frequencies, e.g. of 30 kHz and 40 kHz are used, and shifting takes place at the transmitting side between the two signal frequencies as a function of the modulation. The pulsecode modulation avoids sidebands and continuous frequency swings. The one or the two signal frequencies can be generated at the transmitting side by means of crystal oscillators with a high frequency accuracy and high frequency stability whereas at the receiving side, narrow-banded amplifiers which e.g. are provided with crystal filters and which are tuned to the signal frequence or the signal frequencies, may be provided.

The invention has a multiplicity of advantageous applications.

For example, tachycardiac rhythm disturbances so far at first are treated with drugs. On further progress of the disease, antibradycardiac stimulation by means of a sequential pacemaker of the type known from German unexamined published patent application 27 01 140 may become necessary, wherein simultaneously or at a later state it may be advantageous to supplement the antibradycardiac stimulation by antitachycardiac stimulation pattern (compare e.g., European Patent Specification 0 094 758). When this too is no longer sufficient to adequately influence the syndrome and attacks of ventricular fibrillation occur, a defibrillator becomes necessary which likewise is available as an implantable device. However, when implanting the defibrillator, the sequential pacemaker again must be explanted because this pacemaker delivers atrial and ventricular stimulating pulses which, in the same manner as possibly the R-wave of the electrocardiogram, too, are detected by the defibrillator whereby the latter sees an apparent frequency duplication or frequency triplication. When the heart works correctly with e.g. 70 beats per minute, therefore, there is the risk that the defibrillator detects an apparent heartbeat rate of 140 or 210 beats per minute and undesirably delivers a defibrillation pulse. When the pacemaker is explanted, necessarily the antibradycardiac and possibly also antitachycardiac protective effect thereof no longer exists. Besides, the drug dosage must be reduced because the patient no longer is protected against a drop of the rate of the heart activity. The defibrillator will become active relatively frequently and possibly inappropriately.

Within the scope of the present invention, it is possible to transfer the intelligent decisions, particularly the detection of the requirement of a defibrillation shock, from the defibrillator to the preferably A-V sequential, programmable, microprocessor based pacemaker and to make the defibrillator only indirectly programmable via the pacemaker making use of the body bus. The pacemaker which e.g. may be designed in the manner known from European Patent Specification 0 094 758, safely detects whether the pacemaker itself stimulates or whether there is a tachycardia. When a tachycardia is detected, the pacemaker can request the shock from the defibrillator through the body bus. Therefore, if in the course of the therapy the sequential pacemaker no longer will be sufficient, this pacemaker need not be explanted. Rather the therapy can be systematically built up as a function of the respective requirements without previous implants becoming obsolete. In view of the monitoring functions included in the pacemaker, the requirement of the additional implantation of a defibrillator function can be detected at an early state. The defibrillator, which constitutes a high current application, then can be added. Simultaneously, the sequential antibradycardial stimulation, possibly assisted by drugs, reduces the fibrillation incidence when compared with a pure ventricular stimulation. The stimulation treatment of tachycardia likewise can be carried through by the pacemaker, optionally in a dual chamber manner, whereby the effectivity of detection and of the treatment is increased thereby again reducing the probability of fibrillation. Thus the defibrillator may be restrained, as far as conceivable, to its function as an emergency or backup system.

With respect to the separation of pacemaker and defibrillator, which is easily possible by making use of the body bus, it is to be taken into consideration that the pacemaker, particularly if, in a manner known per se, it is microprocessor controlled and programmable and also includes antitachycardiac algorithms, constitutes a complex and therefore relatively expensive device which, however, merely has a low current consumption and therefore has a very long duration even if the housing volume, as desired, is small. Besides, the pacemaker may be implanted at many different body sites as a function of appropriateness. Different therefrom, a defibrillator has a high energy consumption and, if it was only in view of its storage capacitors, a large volume. It can be implanted at a few body sites only, and in view of its high energy drain, has a relatively short lifetime.

Moreover, recent clinical studies of patients implanted with AICD devices indicate that in a large number of such patients, the defibrillation shock is delivered quite infrequently, i.e. two to four times a year. Despite the infrequent delivery of the shocks, the AICD units need to be replaced within two years due to the deterioration of the batteries. The system of the present invention contemplates the possibility of replacing a large volume, large capacity defibrillator with a small volume low capacity (in other words, a limited number of shocks) in those patients where experience has shown that the patient only infrequently requires a defibrillation shock. It can be expected that in even those patient populations, the frequency of required defibrillation shocks will be diminished by the efficacy of antitachycardia pacing therapies delivered by the separate pacemaker unit.

Thus the present invention contemplates the provision of a staged therapy to the patient first involving the implantation of an intelligent pacemaker in the patient and then, if necessary, the additional implantation of a defibrillator having a shock delivery capacity tailored to the requirements of the patient, e.g. 10, 20, 100 shocks per year at maximum programmable output energy.

In addition, the body bus system components may include separate remote sensors for physiologic rate responsive pacing and/or detection of arrhythmias (to augment or replace the electrogram sensing employed to confirm malignant VT or VF) as well as a drug dispenser. The drug may be delivered into the patient's body or the patient's vascular system as is appropriate to treat the patient in a fashion which the pacemaker electronics would find appropriate. For treatment of an arrhythmia detected by the pacemaker, the drug may be delivered into the vascular system or a chamber of the heart or into the body of the patient in conformance with the appropriate delivery of the specific drug. Therefore, normally it does not make sense to combine the pacemaker and the defibrillator in one and the same casing.

BRIEF DESCRIPTION OF THE DRAWINGS

In the following, the invention is explained in more detail with reference to preferred embodiments thereof.

DESCRIPTION OF THE PREFERRED EMBODIMENTS

Figure 1:
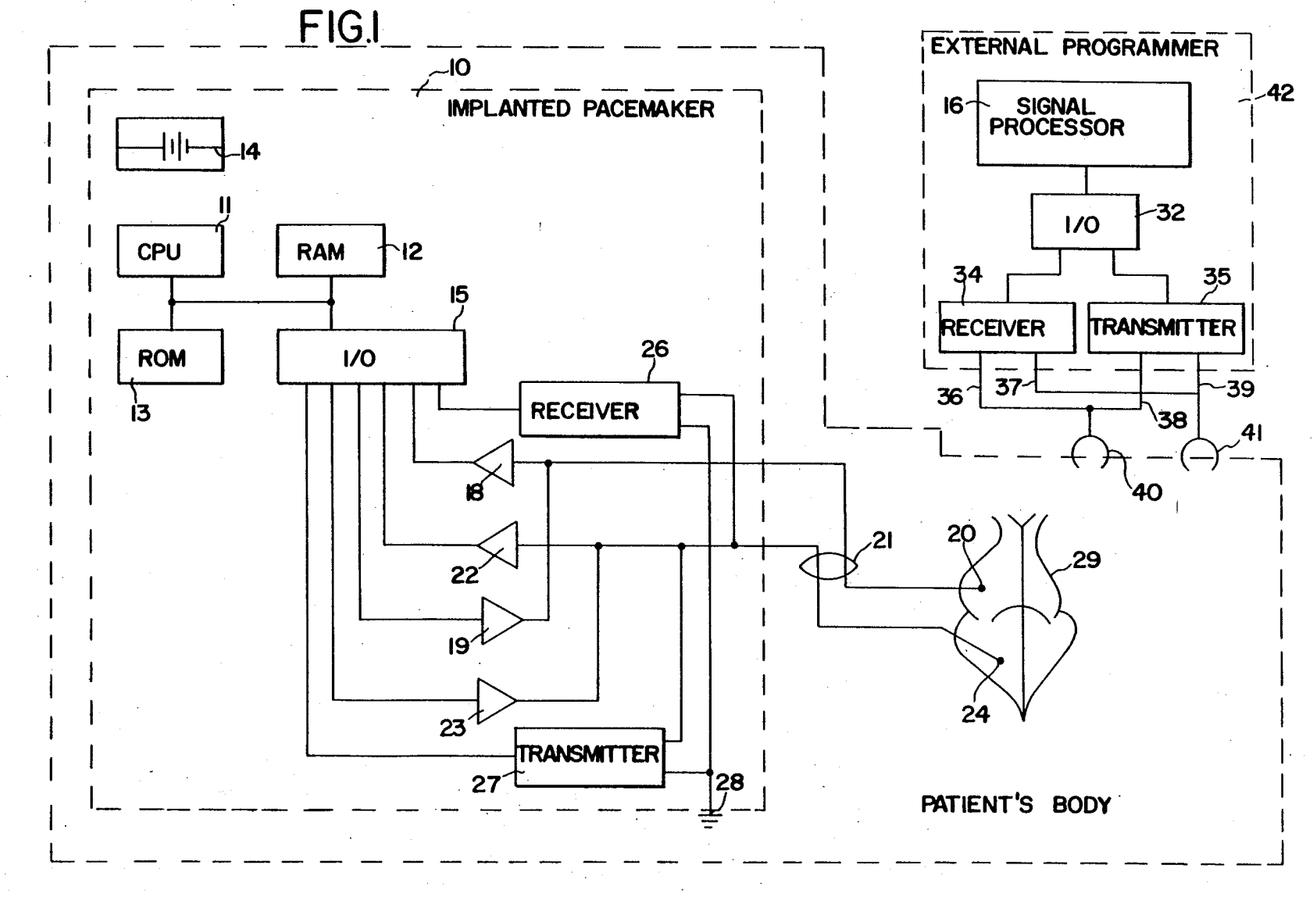
FIG. 1 is a schematic circuit diagram of a cardiac pacemaker adapted for being programmed via the body bus.

FIG. 1 shows an implanted microprocessor controlled, programmable cardiac pacemaker 10 comprising a central processing unit (CPU) 11, a random access memory (RAM) 12, a read-only memory (ROM or EPROM) 13, a battery 14 and an input/output unit (I/0) 15. The input/output unit includes amongst others a coder and a decoder for coding and decoding, respectively, of serial information to be exchanged between the cardiac pacemaker 10 and other implantable or external modules in the illustrated embodiment an external programming unit 42. Such programmable pacemakers and associated programming devices e.g. are known from unexamined published European Patent Application 0 011 935 and European Patent Specification 0 011 936; they, therefore, presently need no further explanation.

The input/output unit 15 is connected through an input or sensing amplifier 18 and an output amplifier 19 to the atrial electrode 20 of a pacemaker lead 21; besides it is connected through an input or sensing amplifier 22 and an output amplifier 23 to a ventricular electrode 24 of the pacemaker lead 21. A body bus receiver 26 is connected to a further input of the input/output unit 15, whereas an additional output of the input/output unit is connected to a body bus transmitter 27. The input of the body bus receiver 26 is connected to the ventricular electrode 24 and to an indifferent electrode 28 which preferably is defined by the casing of the pacemaker 10. The ventricular electrode 24 and the indifferent electrode 28 furthermore are connected to the output of the body bus transmitter 27. The ventricular electrode 24 and the indifferent electrode 28 form a transmitting and receiving dipole for the pacemaker 10. However, the atrial electrode 20 and the indifferent electrode 28 likewise can be used to define the transmitting and receiving dipole of the pacemaker 10. The heart is indicated at 29. The programming signal processor 16 is connected via an input/ output unit 32 to a body bus receiver 34 and to a body bus transmitter. Inputs 36, 37 of the body bus receiver 34 and outputs 38, 39 of the body bus transmitter 35 are connected to external skin electrodes 40 and 41, respectively, which are put around the wrist joints of the patient. The unit 16, together with units 32 to 35, forms an external programming device 42 having a transmitting and receiving dipole defined by electrodes 40 and 41.

Figure 2:
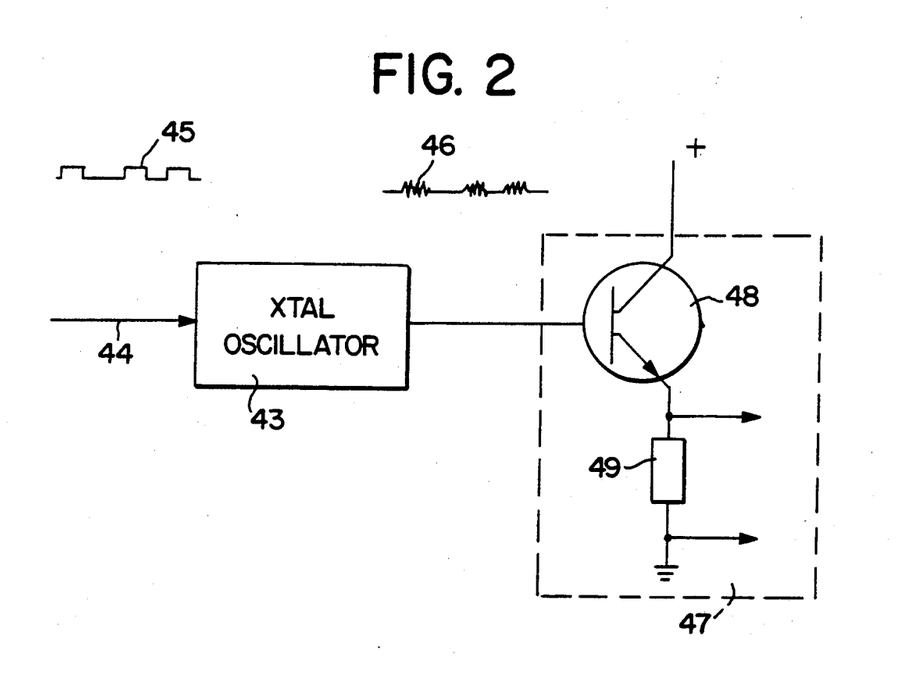
FIG. 2 is a schematic diagram of a busy bus transmitter.

The body bus transmitters 27, 35 may be designed in the manner illustrated in the schematic circuit diagram of FIG. 2. The transmitter includes an oscillator 43, preferably a crystal oscillator, which generates a preferably sinusoidal carrier signal having a fixed predetermined frequency in the medium frequency range extending from 10 kHz to 100 kHz. The oscillator 43 is keyed, in conformity with an Al-modulation, by a serial modulation signal 45 supplied to an input 44. The oscillator correspondingly supplies at its output a modulated medium frequency carrier signal 46 consisting of groups of each a plurality of carrier oscillations. The modulated carrier signal is supplied to the input of an output unit 47 which includes a transistor 48 which delivers across an output resistor 49 an amplified modulated carrier signal having an amplitude of preferably 50 to 500 millivolts, e.g. about 200 millivolts.

Figure 3:
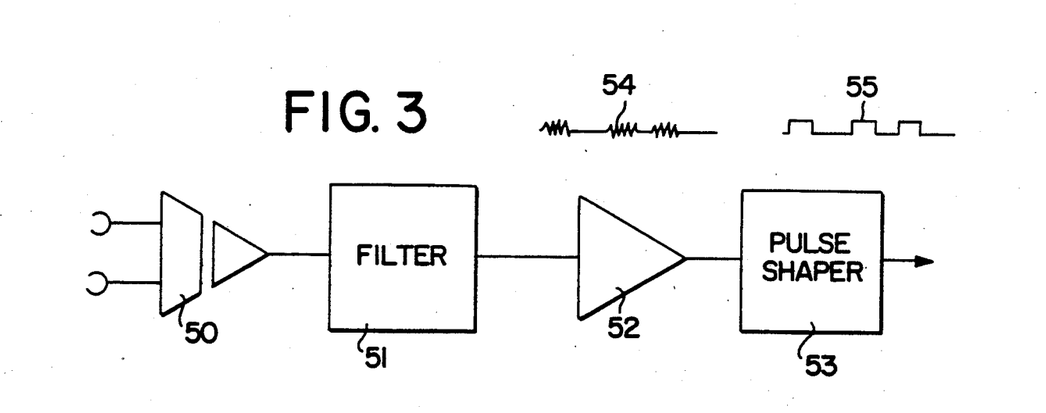
FIG. 3 is a schematic circuit diagram of a body bus receiver.

A design suitable for the body bus receivers 26 and 34 schematically is illustrated in FIG. 3. The receiver, at the input side thereof, includes a preamplifier 50, e.g. an amplifier comprising an octocoupler. Preamplifier 50 is follows by a high-Q filter 51, preferably a crystal filter, which is tuned to the carrier frequency of e.g. 30 kHz. Filter 51 provides a narrow passband for the carrier signal and substantially suppresses signals of all other frequencies. Filter 51 is followed by a further amplifier unit 52 and a demodulator and pulse shaping unit 53 which converts the received filtered groups of carrier signal oscillations 54 into pulses 55 of predetermined amplitude and a duration defined by the code.

Returning to FIG. 1, in order to program the implanted pacemaker, i.e. for setting or changing parameters such as the rate, the amplitude and the width of the stimulation pulses, the sensitivity of the input amplifiers 18, 22, the refractory period, the detection algorithm for detecting arrhythmias (rate, onset/acceleration, number of intervals to trigger, etc.) and the like and/or for selecting one of a plurality of possible pacemaker modes, the electrodes 40, 41 are applied at a desired site of the patient, e.g. at the wrist joints, and serially coded programming commands in the form of the modulated medium frequency carrier signal are supplied to the electrodes 40, 41 from the programming unit 42 via the input/output unit 32 and the body bus transmitter 35. The transmitter dipole defined by electrodes 40, 41 transcutaneously introduces the modulated carrier signal into the body of the patient. There the signal is propagated in the ion medium of the intra and extracellular body liquids. In this manner, the modulated carrier signal is transmitted by electrolytic-galvanic coupling to the receiving dipole defined by the ventricular electrode 24 and the indifferent electrode 28 of the pacemaker 10.

The modulated carrier signal then is amplified, filtered, demodulated and shaped in the body bus receiver 26 and is decoded via input/output unit 15 for further processing. In a corresponding manner the programming device 42 can request from pacemaker 10 information for purposes of monitoring, repeating and remote indicating or the like. This information, again in serially coded form, is communicated from the input/output unit 15 to the body bus transmitter 27 where it modulates a medium frequency carrier signal. The modulated carrier signal is applied by the transmitting dipole defined by electrodes 24, 28 to the ion medium of the body, is propagated there and transcutaneously reaches the electrodes 40 and 41 of the programming device 42 which electrodes now act as a receiving dipole. The modulated medium frequency signal is filtered out in a narrow band mode, is amplified, demodulated and shaped and finally is processed via decoding in input/output unit 32 for being applied to the signal processor unit 16 for decoding, storage and display.

Whereas the transmitters and receivers of FIGS. 2 and 3 are designed for an AI-modulation, other modulation modes, particularly a pulse code modulation with shifting between a pair of carrier signal frequencies within the frequency range from 10 kHz to 100 kHz (so-called FSK-modulation) likewise can be used for the body bus receivers 26, 34 and the body bus transmitters 27, 35.

Figure 4:
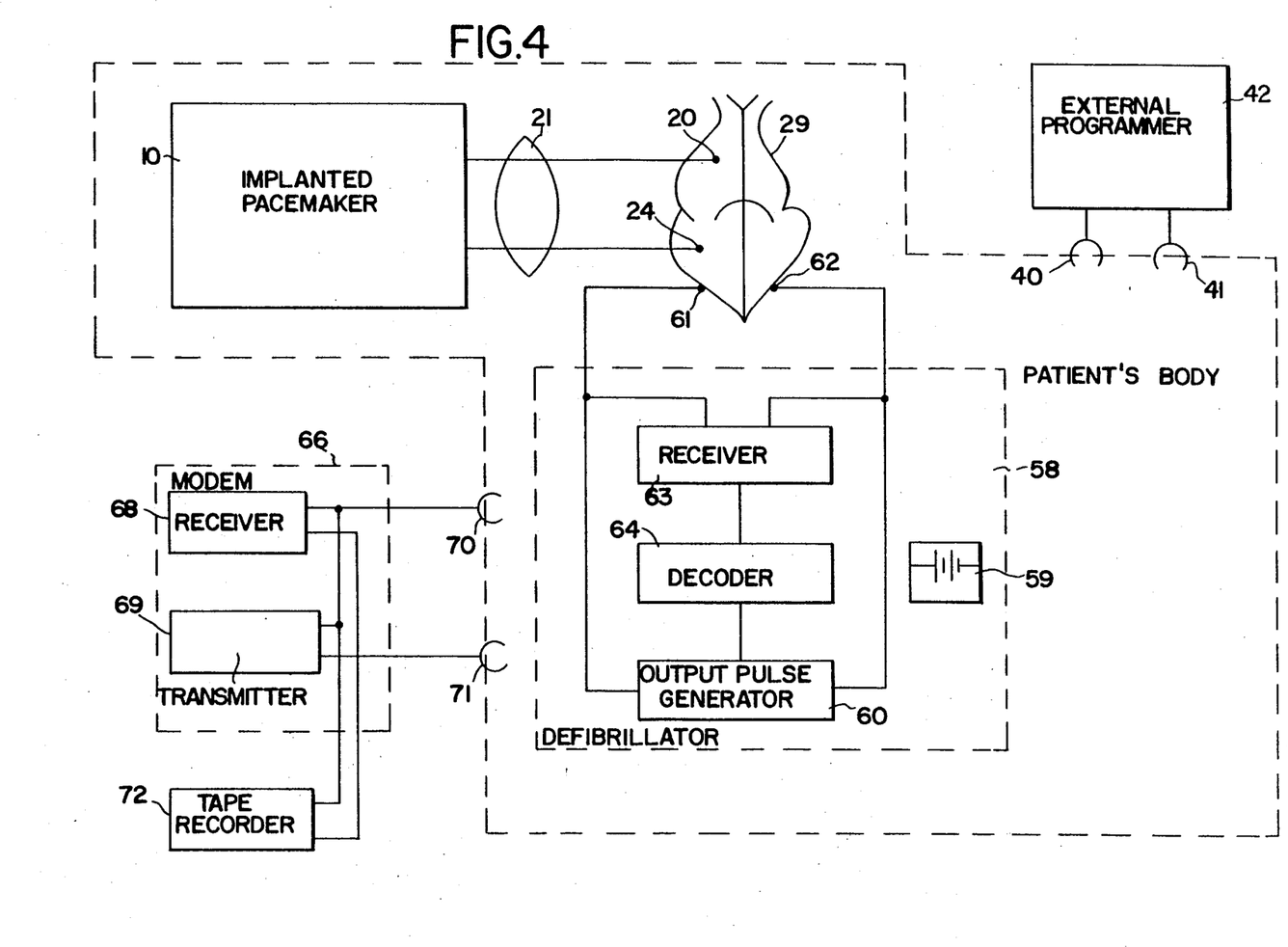
FIGS. 4 and 5 illustrate modified embodiments of devices designed in conformity with the present invention.

The arrangement of FIG. 1, even still afterwards, easily can be further expanded, e.g. by implantation of a defibrillator 58, as schematically illustrated in FIG. 4. The defibrillator 58 comprises a defibrillator output unit 60 adapted to be charged from a battery 59, the output side of unit 60 being connected to implanted defibrillator electrodes 61 and 62. The defibrillator output unit 60, at the input side thereof, is controlled through a body bus receiver 63 and a decoder 64 connected to the output of the latter. The inputs of the body bus receiver 63, which e.g. is designed in conformity with FIG. 3, likewise are connected to the defibrillator electrodes 61, 62 which simultaneously function as receiving dipole of the body bus. The defibrillator 58 together with its associated battery 59 is housed within its own casing, and it can be implanted at a suitable site remote from the pacemaker 10. Defibrillator 58 is controlled by pacemaker 10 which, for this purpose, is provided in a manner known per se (e.g. in conformity with U.S. Pat. No. 4,548,209 and European Patent Specification 0 094 758) with tachycardia and/or fibrillation detection means and, if desired, likewise with means for providing antitachycardiac pacing stimulation pattern, e.g. overdrive, burst or ramp stimulation as is known in the art. In this connection, also means for indirectly programming the defibrillator through the pacemaker 10 and the body bus may be provided. The body bus permits one to intelligently employ the defibrillator 58 which itself does not comprise means for sensing and for making decisions. For example, provisions can be made by a corresponding software design of the microprocessor controlled pacemaker 10 that in case of ventricular tachycardia which cannot be interrupted by means of the pacemaker 10 at first a cardioversion attempt with low energy is caused, whereas in the case of the occurrence of ventricular fibrillation, immediately high energy defibrillation is effected by the defibrillator 58 which is correspondingly controlled by pacemaker 10.

Instead of programming pacemaker 10 by the programming device 42 connected to the skin electrodes, or in addition thereto, programming of pacemaker 10, in conformity with FIG. 4, likewise can be effected through the telephone circuit by means of a simple auxiliary device in form of a modem 66. Modem 66 includes a body bus receiver 68 and a body bus transmitter 69 which, in turn, are connected to external skin electrodes 70 and 71. Modem 66 e.g. can be designed as a modified telephone receiver having a firsthand electrode 70 at the receiver and a separate second wrist joint electrode 71. By a corresponding software design, pacemaker 10 at first can test, with the aid of test signals, the data transport rate of the used telephone network to subsequently automatically adjust the body bus transmitter 69 to the data rate adapted to be communicated. The surface ECG can be directly transmitted to the skin electrodes 70, 71. Selectively, however, it is likewise possible to make sure that all data are communicated through the body bus and that, therefore, the intracardiac ECG is telemetered. Body bus data can be derived through electrodes 70 and 71 for further purposes, e.g. all data which anyway occur in pacemaker 10 can be communicated through the telephone circuit. Data monitoring and keeping of data archives likewise is possible. Thus, in view of the fact that the medium frequency range is used, a tape recorder 72 can be connected to the skin electrodes 40, 41 or 70, 71 in order to record the body bus signals which subsequently can be centrally evaluated by a processor or computer.

Figure 5:
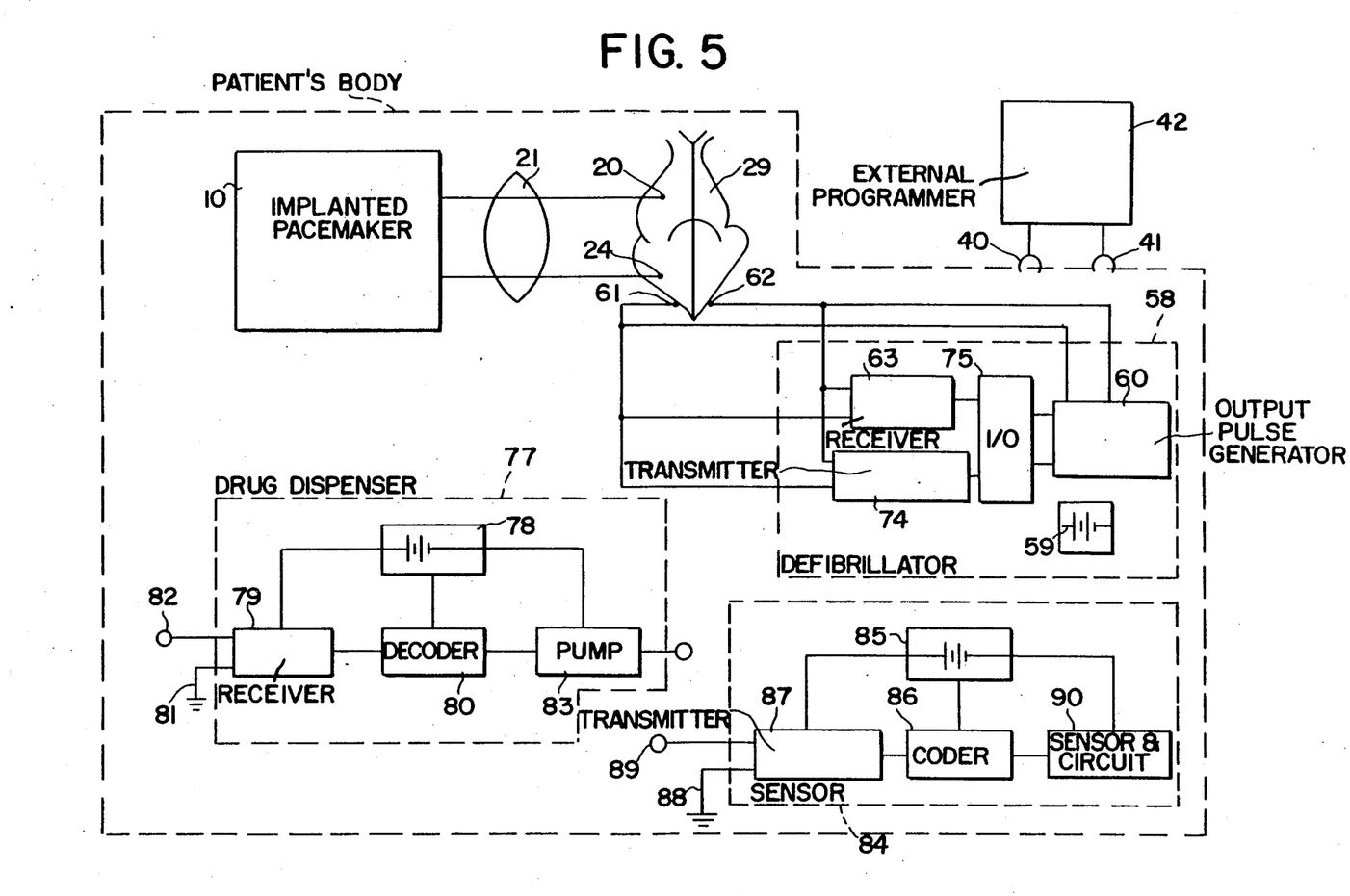

FIG. 5 illustrates a further embodiment in which the defibrillator 58, too, bidirectionally receives and delivers data. For this purpose, a body bus transmitter 74 is provided in addition to the body bus receiver 63. Transmitter 74 and receiver 63 are connected to the defibrillator output unit 60 through an input/output unit 75 which provides for the necessary coding and decoding of the signals. Such a design allows more complicated software structures of the defibrillation protocol. For example, the pacemaker 10, in case of an impending fibrillation, as a precaution, can request the defibrillator 58 to make available a shock which is not delivered to the body until the defibrillator 58 informs the pacemaker that the shock energy is ready. The pacemaker, in response to further monitoring of the heart activity, can decide whether or not the shock is to be delivered to the heart. When the shock, made ready as a precaution, is not required, the pacemaker 10 can deliver a corresponding command to the defibrillator 58, which command causes that the storage capacitor of the defibrillator is slowly discharged or that the energy stored in the storage capacitor is returned through a converter into the defibrillator battery 59, which in this case is rechargeable, in order to save energy. It is also possible that the pacemaker 10 applies possibly dangerous antitachycardiac stimulation modes not before it has made sure through the body bus that in case of an emergency the shock immediately will be available.

FIG. 5 further schematically illustrates an implantable drug delivery device 77 including a battery 78, a body bus receiver 79, a decoder 80 and a drug pump 83. The casing of the device forms a first electrode 81 connected to an input of the receiver 79, whereas a further electrode 82 is connected to a second input of receiver 79. Electrode 82 together with electrode 81 forms an implanted receiving dipole. If required, pacemaker 10 can order, through the body budy, the drug delivery device 77 to deliver a bolus of a drug. Device 77, in a manner similar to defibrillator 58 of FIG. 5, likewise can be designed for a bidirectional exchange of information to allow replies to the pacemaker 10.

FIG. 5 finally illustrates a remote physiologic sensor 84 included in the body bus system, which sensor comprises a battery 85, a coder 86, a body bus transmitter 87 and a sensor and its associated circuitry. An output of the body bus transmitter 87 is connected to a first electrode 88 defined by the sensor casing, whereas a second input of the body bus transmitter 87 is connected to an auxiliary electrode 89. Electrodes 88 and 89 form a transmitting dipole of the sensor. The sensor, in a manner known per se, is adapted to sense respiration body activity or body parameters such as arterial blood pressure, temperature, pH value, pO$_2$ value and the like. Corresponding signals are telemetered to the pacemaker 10 through the body bus for suitably influencing the pacemaker. For example, the sensor data may be used to confirm the existence and nature of a bradyarrhythmia or tachyarrhythmia to influence the selection of the therapy by the pacemaker, drug dispenser or defibrillator and to influence the rate of bradyarrhythmia pacing. The sensor likewise can be designed for a bidirectional exchange of data. In this case it e.g. will be possible to let the pacemaker 10 control sensor characteristics such as the sensitivity of the sensor.

It is evident that the invention can be further modified in many different ways. For example, it is possible to at first implant an AAI pacemaker provided with body bus characteristics. If later on an AV block requires ventricular stimulation, a VVI pacemaker with body bus may be additionally, e.g. myocardially, implanted. The VVI pacemaker and the AAI pacemaker, by exchanging information therebetween, can cooperate to provide for a DDD function.

A further possible application is the implantation of a pacemaker having dp/dt functions for controlling pacing rate as a function of blood pressure rate of change. In such a case, information for delivering from a simultaneously implanted drug delivery device a drug influencing the blood pressure can be transmitted through the body bus. Thereby a 'closed loop' system for blood pressure control is realized.

It is apparent that in each case suitable protocols for the data transmission, for securing priorities, for providing for redundancy and the like, are to be used.

The body bus receivers likewise, in a manner known per se, may be provided with an automatic gain control (AGC).

Figure 6:
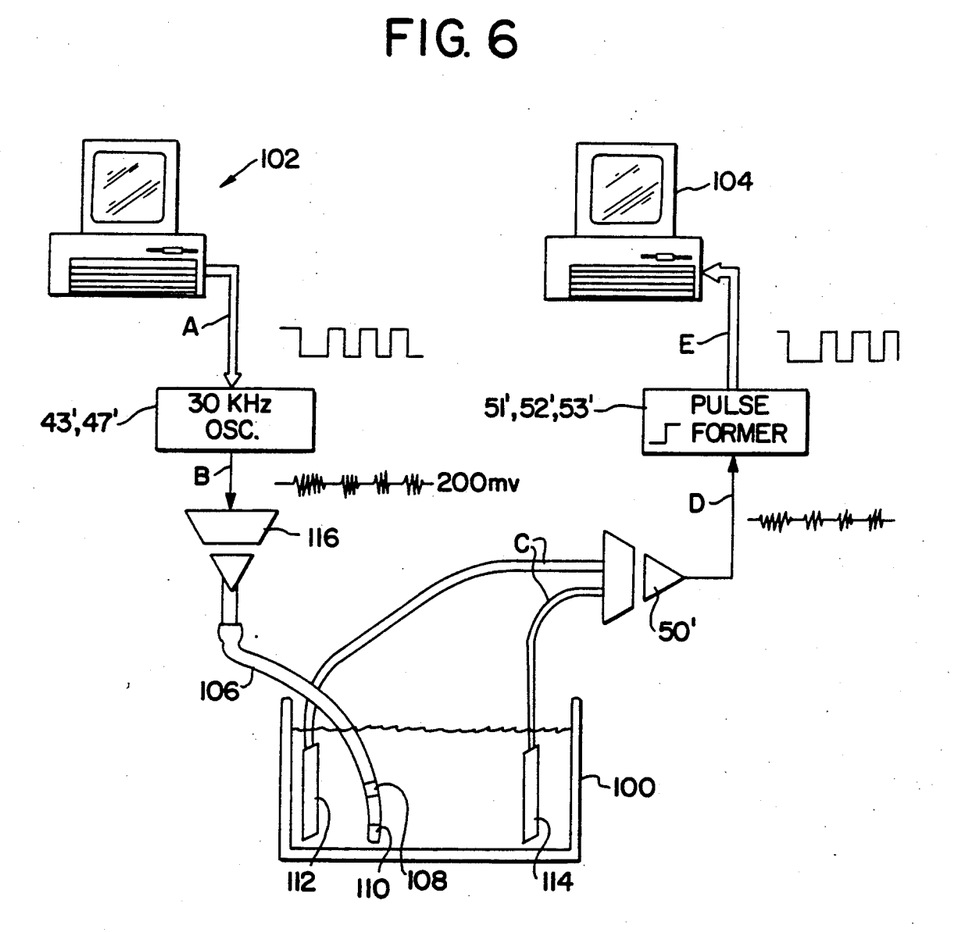
FIG. 6 illustrates the experimental setup prepared to demonstrate body bus signal transmission.

An experimental setup prepared by the inventor to test the practicality of the body bus communication system proposed above is illustrated in FIG. 6 and comprises a physiologic saline test tank 100, two personal computers 102 and 104, a pacing lead 106 having a pair of distal electrodes 108, 110 located within the saline solution, a pair of plate electrodes 112, 114 and transmitting and receiving interconnecting circuitry. The transmitting computer 102 is coupled to the proximal terminals of the pacing lead 106 by the crystal oscillator 43', 47' corresponding to the transmitter circuit of FIG. 2 and a further optocoupler 116. Similarly, the plate electrodes 112 and 114 are coupled to the two inputs of an optocoupler and preamplifier 50', the output of which is coupled to the pulse former circuitry 51', 52', 53' which collectively correspond to the receiver circuit of FIG. 3. The output signal of the pulse former 51', 52', 53' is applied to the second personal computer 104.

The plate electrodes 112 and 114 were prepared from copper plates each having a surface of approximately 64cm$^2$ to electrically imitate one type of implantable defibrillator leads. The electrodes 112, 114 are placed apart a distance approximating the distance that defibrillating plate electrodes are normally spaced across the heart in actual implantations in patients. The standard endocardial bipolar pacing lead 106 is placed so that its bipolar electrodes 108, 110 are between the plate electrodes 112, 114 to approximate the location within a patient's heart. The tank 100 is filled with physiological saline solution. The experiments were conducted to test the hypothesis that useful information could be transmitted in both directions through the conducting medium between the pacing electrodes 108, 110 and the defibrillation electrodes 112, 114.

With the 8032 based Commodore personal computer, text was entered by its keyboard which is converted into the corresponding ASCII-NR. code which is written as an 8-bit byte into a memory location. This byte is then converted into a serial train of bit pulses preceded by a leader pulse and is emitted from its cassette port so as to gate the output of the signal generator 43', 47' at 30- kHz. With an appropriate level (200 mV) these 30 kHz burst pulses are fed through the optocoupler 116 to a Medtronic bipolar Model 6901 lead 106 immersed in the physiologic saline solution. The signals are shown illustrated at points A and B in FIG. 6, the leader illustrated as the initial wide burst signal. Pulse width modulation was employed to encode the stream of bits emitted by the electrodes 108, 110 into the saline solution.

The signals emitted from the bipolar pacing electrodes 108, 110 travel through the saline solution and are picked up by the defibrillator electrodes 112, 114 and applied to the input terminals of the optocoupler in preamplifier 50'. The signal level at the input terminals of the optocoupler amplifier 50' is approximately 3 mV. After filtering and amplification by the optocoupler preamplifier 50' and pulse former 51', 52', 53', the lower edge envelope curve is reconstructed so that at this stage, the serial 8 bit pulse train with its leader can be applied to an input port or user port of a second 8032 Commodore personal computer. After serial to parallel conversion, the received code is displayed on the computer screen.

During testing, the removal of the pacing lead 106 from the saline solution during transmission of the code between the transmitting computer 102 and receiving computer 104 interrupted and terminated the transmission. Thus the transmission is obtained by the bulk conductivity of the saline solution. Moreover, by reversing the electrode connections, information could just as easily be transferred from the defibrillator plate electrodes as the transmitting electrodes to the pacing electrodes 108, 110. Various experiments were conducted with the orientation of the electrodes 108, 110 to the electrodes 112 and 114 wherein it was found that the only orientation that became insufficient was when the transmitting dipole provided by the pacing electrodes 108, 110 was directly perpendicular to the receiving dipole provided by the electrodes 112, 114 (or conversely). With conformal defibrillation electrodes 112, 114 and the usual orientation of a bipolar pacing lead axially within the heart's right ventricle, it is unlikely that this insufficient orientation would be encountered in practice.

A second bipolar electrode was connected to the output and can of a Medtronic Model 8423 VVI pacemaker which was also put into the bath of saline in tank 100. The pacemaker could not be inhibited by the high frequency 30 kHz bursts being delivered through the saline medium. This test confirmed the proposition that the 30 kHz signal at the 200 mV amplitude did not mimic signals normally sensed by a pacemaker and thereby interfere with its normal operation. The waveform used, even switched at rates at about 80 bpm, would not inhibit a standard VVI pacemaker.

In tests conducted with this experimental setup, it was determined that the burst pulse modulation with a carrier in the range of 30 kHz enabled the propagation of ASCII code safely, easily and rapidly through the conductive medium of the test tank 100. The frequency and voltage related current levels employed allow for the use of already implanted heart stimulation leads without the need of synchronization into the refractory periods of the pulse generators. Since there are no side bands, extremely narrow pass amplification of the received signals would make electrical noise suppression very simple. The baud rate can exceed 400 bauds. Since the transmission speed is higher than any imaginable intracorporeal need, a high degree of safety can be achieved by redundant transmission and other forms of data encription.

A computer listing actually used to transmit the statement 'the quick brown fox jumps over the lazy dog' between the transmitting and the receiving personal computers is attached hereto as follows:

```
START OF TRANSMITTER (BASIC)
100 rem name of program: 12b transmit.
105 rem purpose: transmitting ascii code for bodybus.
110 rem principle:  parallel to serial conversion ('lsr')
115 rem             and keying of a 30 kHz oscillator thru
120 rem             cassette port #2 of a commodore
125 rem             computer.
130 rem             the oscillator output (bursts, 30 kHz,
135 rem             200 mV) is conducted into .9% saline
                    by a Medtronic 6901 bipolar lead.
140 if peek (19999)<>17then poke 19999,17:load"12m transmit",8,1
145 poke 20006,12:poke20029,3:poke20037,6:poke20093,3:rem increments in lms
150 sys63739:poke59456,227:rem initializing cassette port #2 for transmission
115 y$="-----The quick brown fox jumps over the lazy dog 1 2 3 4 5 6 7 8 9 0"
160 fora=1to68:b$=mid$(y$,a,1):gosub185:nexta:print
165 b=13:gosub190
170 print"More code entered by keyboard.":print
175 getb$:1fb$=""""then175:rem get input from keyboard
180 gosub185:goto175
185 b=asc(b$)
190 printchr$(b);:poke20003,b:sys20004:return:rem transmit ascii-#
END OF TRANSMITTER (BASIC)
START OF TRANSMITTER (ASSEMBLY 6502)
20000 nop
20001 nop
20002 nop
20003 brk
20004 sei
20005 lda 12
20007 stam 20055
20010 jsr 20054
20013 jsr 20092
20016 ldx 8
20018 ldam 20003
20021 clc
20022 lsr
20023 stam 20003
20026 bcs 20036
20028 lda 3
20030 stam 20055
20033 jmp 20041
20036 lda 6
20038 stam 20055
20041 jsr 20054
20044 jsr 20092
20047 dex
20048 bne 20018
20050 cli
20051 rts
20052 brk
20053 brk
20054 lda 3
20056 stam 20052
20059 lda 243
20061 stam 59456
20064 lda 75
20066 stam 20053
20069 decm 20053
20072 nop
20073 nop
20074 bne 20069
20076 decm 20052
20079 bne 20064
20081 lda 227
20083 stam 59456
20086 rts
20087 nop
20088 nop
20089 nop
20090 brk
20091 brk
20092 lda 3
20094 stam 20090
20097 lda 75
20099 stam 20091
20102 decm 20091
20105 nop
20106 nop
20107 bne 20102
20109 decm 20090
20112 bne 20097
20114 rts
END OF TRANSMITTER (ASSEMBLY 6502)
```

```
START OF RECEIVER (BASIC)
100 rem name of program: 12b receiver
105 rem purpose:    receive and decode ascii code for
110 rem principle:  bodybus amplification, filtering,
111 rem             pulse forming and decoding ('ror').
112 rem             The signals (bursts, 30 kHz, .6mV) are
113 rem             received through 2 copper plates
114 rem             immersed in .9% saline, surface each
                    ca. 64 sq. cm.
115 ifpeek(19999)<>17thenpoke19999,17:load"12m
receiver",8,1
120 poke20016,8:poke20087,4:rem speed intervals in ms
125 sys20000:rem start of 12m receiver
130 printchr$(peek(20063));:rem print received character
on screen
135 go to 125
END OF RECEIVER (BASIC)
START OF RECEIVER (ASSEMBLY 6502)
20000 sei
20001 lda 1
20003 bitm 59471
20006 bne 20001
20008 jmp 20015
20011 nop
20012 nop
20013 brk
20014 brk
20015 lda 8
20017 stam 20013
20020 lda 75
20022 stam 20014
20025 lda 1
20027 bitm 59471
20030 bne 20045
20032 decm 20014
20035 bne 20025
20037 decm 20013
20040 bne 20020
20042 jmp 20050
20045 cli
20046 rts
20047 nop
20048 nop
20049 nop
20050 lda
20052 bitm 59471
20055 beg 20050
20057 jmp 20067
20060 nop
20061 nop
20062 nop
20063 oram 10753
20066 brk
20067 ldx 8
20069 lda 255
20071 stam 20066
20074 decm 20066
20077 bne 20074
20079 lda 1
20081 bitm 59471
20084 bne 20079
20086 lda 4
20088 stam 20064
20091 lda 57
20093 stam 20065
20096 lda 1
20098 bitm 59471
20101 bne 20116
20103 decm 20065
20106 bne 20096
20108 decm 20064
20111 bne 20091
20113 jmp 20127
20116 clc
20117 ldam 20063
20120 ror
20121 stam 20063
20124 jmp 20142
20127 sec
20128 ldam 20063
20131 ror
20132 stam 20063
20135 lda 1
20137 bitm 59471
20140 beg 20135
20131 dex
20143 bne 20069
20145 cli
20146 rts
END OF RECEIVER (ASSEMBLY 6502)
```

From the foregoing description, it will be apparent that the body bus system of the present invention has a number of advantages, some of which have been described above and others of which are inherent in the invention. Also it will be apparent that modifications can be made to the system without departing from the teachings of the present invention. Accordingly, the scope of the invention is only to be limited as necessitated by the accompanying claims.

What is claimed is:

1. In a system for monitoring a condition of a living body and/or providing one or more therapy regimens to the body comprising two or more discrete medical devices, at least one of which is implanted into the living body, the improvement for providing bidirectional exchange of information between said medical devices comprising:
   means associated with at least one of said medical devices for providing a first information signal representing a condition of the device and/or the living body;
   means for transforming said first information signal into a modulated medium frequency signal in the frequency range from 10 to 100 kHz;
   means for applying said modulated medium frequency signal to the ion medium of the intra and extracellular body liquids for providing an electrolytic/galvanic coupling between said two or more medical devices whereby said signals are passed through said living body between said medical devices; and
   means associated with at least the other of the two medical devices for receiving and demodulating said modulated medium frequency signal.

2. The system according to claim 1 wherein said medium frequency signal is modulated at 30 kHz.

3. The system according to claim 1 characterized in that a cardiac pacemaker is provided as an implantable medical device.

4. The system according to claim 3 characterized in that a defibrillator, which is separate from said cardiac pacemaker, is provided as a further implantable medical device.

5. The system according to claim 4 characterized in that both said cardiac pacemaker and said defibrillator are provided with transmitting and receiving means.

6. The system according to claim 3 characterized in that in case a plurality of implantable medical devices are provided, programming and/or intelligent decision means are concentrated in said cardiac pacemaker and that other medical devices are indirectly programmable via said cardiac pacemaker.

7. The system according to claim 1 characterized in that in case a plurality of implantable medical devices are provided, programming and/or intelligent decision means are concentrated in only one of the implantable medical devices and that other medical devices are indirectly programmable via said only one implantable medical device.

8. The system according to claim 1 characterized in that a drug delivery device is provided as an implantable medical device.

9. The system according to claim 1 characterized in that a sensor for detecting a body parameter is provided as an implantable medical device.

10. The system according to claim 1 characterized in that a controllable and/or programmable artificial organ is provided as an implantable medical device.

11. The system according to claim 1 characterized in that a monitoring or test device is provided as an external medical device.

12. The system according to claim 11 characterized in that a modem adapted for connection to a telephone circuit is provided as an external medical device.

13. The system according to claim 12 characterized in that a data recording device is provided as an external medical device.

14. The system according to claim 1 characterized in that the medical devices are provided with means for receiving and/or transmitting of pulsecode-modulated medium frequency signals.

15. The system according to claim 1 characterized in that the medical devices are provided with means for receiving and/or transmitting Al-modulated medium frequency signals.

16. The system according to claim 1 characterized in that the medical devices are provided with means for receiving and/or transmitting signals which are frequencyshifted between a pair of frequencies within the medium frequency range.

17. The system according to claim 1 characterized in that the modulated medium frequency signals have an amplitude from 50 to 500 millivolts and a frequency of 30 kHz.

18. The system according to claim 1 further comprising:
- at least one digitally programmable, implantable medical device and an external medical device for digitally programming said implantable medical device wherein said implantable medical device is provided with: a pair of spaced apart electrodes adapted to be exposed to living body tissue and fluids;
- receiving means for receiving electrical signals across said electrodes;
- decoding means for decoding said electrical signals; and
- register means for storing said decoded electrical signals; and
- wherein said digital programming device further comprises:
- a pair of electrodes adapted to be placed against the external surface of said living body;
- coding means for coding a desired program change into digital code; and
- transmitting means for modulating said programmed digital code and applying it to said external pair of electrodes whereby said modulated medium frequency signal in the frequency range from 10 to 100 kHz is applied through the skin and living body tissue to said implantable pair of electrodes.

19. The system according to claim 1 wherein a first body implantable medical device comprises means for providing a therapy to the living body and wherein a second medical device comprises a remotely implanted physiological body condition detecting device and further includes:
- sensor means for sensing a physiological parameter in said body;
- signal converting circuit means for converting signals generated by said sensor means to modulated medium frequency signals in the frequency range from 10 to 100 kHz;
- a first pair of spaced-apart electrodes adapted to be placed in contact with the body tissue within the living body;
- transmitting means for transmitting said modulated signal to said first medical device by applying said modulated signal across said first spaced apart implanted electrodes; and
- wherein said first medical device further comprises:
- a second pair of spaced-apart electrodes implanted within the living body in contact with body tissue; and
- receiving means coupled to said second pair of electrodes for demodulating and decoding said signal transmitted from said first medical device.

20. A system for monitoring a condition of a living body and/or providing one or more therapy regimens to the body comprising two or more discrete medical devices, at least one of which is a digitally programmable, implantable medical device and the other is an external medical device for digitally programming said implantable medical device wherein said implantable medical device is provided with:
- a pair of spaced apart electrodes adapted to be exposed to living body tissue and fluids;
- receiving means for receiving electrical signals across said electrodes;
- decoding means for decoding said electrical signals; and
- register means for storing said decoded electrical signals; and
- wherein said digital programming device further comprises:
- a pair of electrodes adapted to be placed against the external surface of the living body;
- coding means for coding a desired program change into digital code; and
- transmitting means for modulating said programmed digital code and applying it to said external pair of electrodes whereby said modulated, coded signal is applied through the skin and living body tissue to said implantable pair of electrodes.

21. The system according to claim 20 wherein said body implantable medical device comprise means for providing a therapy to the living body, and the system includes a further body implantable medical device comprising a remotely implanted physiological body condition detecting device including:
- sensor means for sensing a physiological parameter in the body;
- signal converting circuit means for converting signals generated by said sensor means to modulated signals;
- a first pair of spaced-apart electrodes adapted to be placed in contact with the body tissue within the living body;
- transmitting means for transmitting said modulated signals to said first medical device by applying said modulated signals across said first spaced apart implanted electrodes; and wherein said first implantable medical device further comprises:
a second pair of spaced-apart electrodes implanted within the living body in contact with body tissue; and
receiving means coupled to said second pair of electrodes for demodulating and decoding signals transmitted from said first medical device.

22. The system according to claim 21 wherein said first implantable medical device further comprises:
means for providing a control signal for controlling the operation of said sensor means of said further body implantable medical device;
means for coding said control signal;
transmitting means for transmitting said coded control signal to said further medical device by applying said coded control signal across said second pair of electrodes;
wherein said further body implantable medical device further comprises receiver means coupled to said first pair of spaced apart electrodes for receiving electrical signals appearing across said electrodes;
decoding means for decoding said electrical signals; and
register means for storing said decoded control signals, whereby the operating condition of said sensor means may be remotely controlled by said first body implantable medical device.

23. The system according to claim 22 wherein said digitally programmable, implantable medical device, said further body implantable medical device and said external medical device each respectively transmit and receive modulated medium frequency signals in the frequency range from 10 to 100 kHz.

24. The system according to claim 21 wherein said sensor means for sensing a physiological parameter in a body comprise means for sensing one or more of the body conditions including respiration, body activity or body parameters including arterial blood pressure, rate of change of blood pressure, temperature, pH value, pO$_2$ value.

25. A system for providing pacing, cardioversion and defibrillation staged therapies for bradycardia, tachycardia and fibrillation comprising:
a body implantable pacemaker comprising:
pacing energy pulse generator means for applying pacing stimuli to a patient's heart;
pacing lead means bearing at least one electrode means adapted to be placed in contact with or within a patient's heart and coupled to said pulse generator means for applying said pacing stimuli to the patient's heart and receiving electrical signals appearing at the tissue-electrode interface;
sensing means coupled to said electrode means for sensing electrical signals appearing at said electrode means;
detecting means responsive to said sensing means for detecting a bradyarrhythmia, tachyarrhythmia or ventricular fibrillation condition of the heart of the patient; and
control means responsive to said detecting means for instructing said pulse generator means to provide pacing stimuli to said pacing electrode means in response to the detection of a bradyarrhythmia or tachyarrhythmia condition and to provide a modulated medium frequency signal in the frequency range from 10 to 100 kHz to said pacing electrode means in response to the detection of a ventricular fibrillation condition; and
a remotely implanted defibrillator further comprising:
defibrillation pulse generator means for generating defibrillation shocks;
defibrillation electrode means adapted to be placed in contact with a patient's heart for providing said defibrillation shocks to the heart and for picking up electrical signals appearing at the electrode-tissue interface;
receiving means coupled to said defibrillation electrode means for demodulating said modulated medium frequency signal transmitted into body tissue by said pacemaker pulse generator; and
means responsive to a demodulated shock instruction signal for causing said defibrillation pulse generator means to provide a shock across said defibrillation electrode means and to the heart.

26. The system according to claim 25 wherein:
said defibrillator further comprises:
transmitting means coupled to said defibrillation electrode means;
coding means for coding data representing the condition of the defibrillator for providing further coded data to said transmitting means comprising means for transforming said coded signal into a modulated medium frequency signal in the frequency range from 10–100 kHz and means for applying said modulated medium frequency signals to said defibrillation electrode means; and
said pacemaker further comprises:
means coupled to said sensing means for demodulating and decoding said further coded data; and
said control means comprises means responsive to said further coded data for providing instructions to said defibrillator.

27. The system according to claim 25 or 26 wherein said medium frequency signal is modulated at 30 kHz.

28. The system according to claim 25 or 26 characterized in that the pacemaker and defibrillator are provided with means for receiving and/or transmitting of pulsecode-modulated medium frequency signals.

29. The system according to claim 25 or 26 characterized in that the pacemaker and defibrillator are provided with means for receiving and/or transmitting Al-modulated medium frequency signals.

30. The system according to claim 25 or 26 characterized in that the pacemaker and defibrillator are provided with means for receiving and/or transmitting signals which are frequency-shifted between a pair of frequencies within the medium frequency range.

31. The system according to claim 25 or 26 characterized in that the modulated medium frequency signals have an amplitude from 50 to 500 millivolts and a frequency of 30 kHz.

* * * * *